United States Patent
Altwasser et al.

(10) Patent No.: US 8,901,320 B2
(45) Date of Patent: Dec. 2, 2014

(54) PROCESS FOR CONTROLLING A GAS PHASE OXIDATION REACTOR FOR PREPARATION OF PHTHALIC ANHYDRIDE

(75) Inventors: Stefan Altwasser, Wachenheim (DE); Jürgen Zühlke, Speyer (DE); Hao Chen, Pictorial Garden (CN); Cornelia Katharina Dobner, Ludwigshafen (DE); Frank Rosowski, Mannheim (DE)

(73) Assignee: BASF SE (DE)

( * ) Notice: Subject to any disclaimer, the term of this patent is extended or adjusted under 35 U.S.C. 154(b) by 232 days.

(21) Appl. No.: 13/085,537

(22) Filed: Apr. 13, 2011

(65) Prior Publication Data

US 2011/0251405 A1 Oct. 13, 2011

Related U.S. Application Data

(60) Provisional application No. 61/323,409, filed on Apr. 13, 2010.

(51) Int. Cl.
C07D 307/89 (2006.01)

(52) U.S. Cl.
CPC .................................. *C07D 307/89* (2013.01)
USPC ........................................ 549/248; 549/247

(58) Field of Classification Search
USPC ......................................................... 549/248
See application file for complete search history.

(56) References Cited

U.S. PATENT DOCUMENTS

| | | | |
|---|---|---|---|
| 4,141,909 A | 2/1979 | Wiedemann et al. | |
| 4,284,571 A | 8/1981 | Sato et al. | |
| 4,481,304 A | 11/1984 | Sato et al. | |
| 5,792,719 A | 8/1998 | Eberle et al. | |
| 5,969,160 A | 10/1999 | Lindstrom | |
| 6,288,273 B1 | 9/2001 | Heidemann et al. | |
| 6,362,345 B1 | 3/2002 | Heidemann et al. | |
| 6,528,683 B1 | 3/2003 | Heidemann et al. | |
| 6,586,361 B1 | 7/2003 | Heidemann et al. | |
| 6,700,000 B1 | 3/2004 | Heidemann et al. | |
| 7,151,184 B2 | 12/2006 | Storck et al. | |
| 7,371,893 B2 | 5/2008 | Storck et al. | |
| 2006/0276661 A1 | 12/2006 | Storck et al. | |
| 2007/0060758 A1 | 3/2007 | Storck et al. | |
| 2007/0135302 A1 | 6/2007 | Neto et al. | |
| 2009/0005908 A1* | 1/2009 | Butoyi ........................... | 700/266 |
| 2009/0163726 A1 | 6/2009 | Wilmer et al. | |
| 2009/0286999 A1 | 11/2009 | Wilmer et al. | |
| 2009/0306409 A1 | 12/2009 | Guckel et al. | |
| 2009/0312562 A1 | 12/2009 | Guckel et al. | |
| 2009/0318712 A1 | 12/2009 | Wilmer et al. | |
| 2010/0069659 A1 | 3/2010 | Raichle et al. | |
| 2010/0069660 A1 | 3/2010 | Raichle et al. | |
| 2011/0028740 A1 | 2/2011 | Dobner et al. | |
| 2011/0034707 A1 | 2/2011 | Wilmer et al. | |
| 2011/0118487 A1 | 5/2011 | Abdallah et al. | |
| 2011/0124885 A1 | 5/2011 | Altwasser et al. | |
| 2011/0130273 A1 | 6/2011 | Karpov et al. | |
| 2011/0144387 A1 | 6/2011 | Wentink et al. | |
| 2011/0152433 A1 | 6/2011 | Bechtloff et al. | |
| 2011/0163278 A1 | 7/2011 | Domke et al. | |
| 2011/0195347 A1 | 8/2011 | Querner et al. | |
| 2011/0206753 A1 | 8/2011 | Karpov et al. | |
| 2011/0230668 A1 | 9/2011 | Altwasser et al. | |
| 2011/0245392 A1 | 10/2011 | Karpov et al. | |
| 2011/0250124 A1 | 10/2011 | Kramer et al. | |
| 2011/0251052 A1 | 10/2011 | Kramer et al. | |
| 2011/0251405 A1 | 10/2011 | Altwasser et al. | |
| 2011/0257413 A1 | 10/2011 | Dobner et al. | |
| 2011/0257414 A1 | 10/2011 | Dobner et al. | |
| 2012/0004425 A1 | 1/2012 | Altwasser et al. | |
| 2012/0043537 A1 | 2/2012 | Karpov et al. | |
| 2012/0071671 A1 | 3/2012 | Karpov et al. | |
| 2012/0077998 A1 | 3/2012 | Seeber et al. | |
| 2012/0086002 A1 | 4/2012 | Fleischhaker et al. | |

(Continued)

FOREIGN PATENT DOCUMENTS

| | | |
|---|---|---|
| CN | 1635989 | 7/2005 |
| DE | 1269119 B | 5/1968 |

(Continued)

OTHER PUBLICATIONS

U.S. Appl. No. 13/052,140, filed Mar. 21, 2011, Altwasser et al.
U.S. Appl. No. 13/083,055, filed Apr. 8, 2011, Krämer et al.
U.S. Appl. No. 13/084,934, filed Apr. 12, 2011, Krämer et al.
Anastasov, A. I., "Deactivation of an industrial $V_2O_5$—$TiO_2$ catalyster for oxidation of o-xylene into phthalic anhydride," Chemical Engineering and Processing, 2003, vol. 42, pp. 449-460.
Bond, G. C., "What Limits the Selectivity Attainable in the Catalysed Oxidation of o-Xylene to Phthalic Anhydride?" J. Chem. Tech. Biotechnol., 1997, vol. 68, pp. 6-13.

(Continued)

*Primary Examiner* — Samantha Shterengarts
*Assistant Examiner* — Amanda L Aguirre
(74) *Attorney, Agent, or Firm* — Drinker Biddle & Reath LLP

(57) ABSTRACT

In a process for controlling a gas phase oxidation reactor for preparation of phthalic anhydride, by passing a gas stream which comprises an aromatic hydrocarbon and molecular oxygen through a multitude of reaction tubes arranged in the gas phase oxidation reactor, each of which comprises a bed of at least one catalyst and the temperature of which can be controlled by means of a heat transfer medium, at least one control parameter is measured and correcting interventions for control of the control parameter are determined, the at least one control parameter comprising the phthalic anhydride yield and the correcting parameter used being the temperature of the heat carrier medium. Over at least 90% of the lifetime of the catalyst, the change in the correcting parameter is limited to a maximum of 0.5 K within a period of 30 days. In this way, the cumulated phthalic anhydride yield over the lifetime of the catalyst is maximized.

8 Claims, No Drawings

(56) References Cited

U.S. PATENT DOCUMENTS

| | | |
|---|---|---|
| 2012/0097068 A1 | 4/2012 | Riggs et al. |
| 2012/0106139 A1 | 5/2012 | Ewald et al. |
| 2012/0108713 A1 | 5/2012 | Ewald et al. |
| 2012/0149919 A1 | 6/2012 | Altwasser et al. |

FOREIGN PATENT DOCUMENTS

| | | |
|---|---|---|
| DE | 2005969 A1 | 8/1971 |
| DE | 2948163 A1 | 6/1980 |
| DE | 4006935 A1 | 9/1991 |
| DE | 4109387 A1 | 9/1992 |
| DE | 19807018 A1 | 8/1998 |
| DE | 19824532 A1 | 12/1999 |
| DE | 19839001 A1 | 3/2000 |
| EP | 286448 A2 | 10/1988 |
| EP | 522871 A1 | 1/1993 |
| EP | 539878 A2 | 5/1993 |
| EP | 0 744 214 A1 | 11/1996 |
| EP | 1082317 A1 | 3/2001 |
| EP | 1084115 A1 | 3/2001 |
| EP | 1091806 A1 | 4/2001 |
| EP | 1636161 A1 | 3/2006 |
| EP | 2009520 A1 | 12/2008 |
| WO | WO-2004103561 A1 | 12/2004 |
| WO | WO-2004103943 A1 | 12/2004 |
| WO | WO-2005/030388 A1 | 4/2005 |
| WO | WO-2006125468 A1 | 11/2006 |
| WO | WO-2007/116018 A1 | 10/2007 |
| WO | WO-2007116018 A1 | 10/2007 |
| WO | WO-2007134849 A1 | 11/2007 |
| WO | WO-2010/136551 A2 | 12/2010 |
| WO | WO-2011/080051 A1 | 7/2011 |

OTHER PUBLICATIONS

Galantowicz, M., et al., "Effect of thermal deactivation of vanadium—titanium catalyst on o-xylene oxidation process yielding phthalic anhydride," Studies in Surface Science and Catalysis, 1994, vol. 88, pp. 591-596.
U.S. Appl. No. 13/518,768.
Stanislaw E. Golunski et al., "Antimony Oxides : a Guide to Phase Changes During Catalyst Preparation", Applied Catalysis, vol. 48, pp. 123-135, 1989.
U. A. Schubert et al., "Possible effects of site isolation in antimony oxide-modified vanadia/titania catalysts for selective oxidation of o-xylene", Topics in Catalysis, vol. 15, No. 24, pp. 195-200, 2001.
Christer Svensson, "Refinement of the Crystal Structure of Cubic Antimony Trioxide, $Sb_2O_3$", Aeta Cryst., vol. B31, pp. 2016-2018, 1975.
Howard E.Swanson et al., "Standard X-ray Diffraction Powder Patterns", National Bureau of Standards Circular 539, vol. 10, pp. 6-8, 1960.
International Search Report from companion PCT/EP2010/067432 of Nov. 15, 2010.
International Search Report from PCT/IB2011/053327 dated Jan. 5, 2012.
International Search Report for PCT/IB2011/052831.
Anastasov, A. I., "Deactivation of an industrial $V_2O_5$—$TiO_2$ catalyster for oxidation ofoxylene into phthalic anhydride," Chemical Engineering and Processing, 2003, vol. 42, pp. 449-460.
Garcin, et al., "Preparation of $V_2O_5/TiO_2$ Eurocat oxide catalysts," *Catalysis Today* 20 (1994), pp. 7-10.
Grzybowska-Świerkosz, "Vanadia-titania catalysts for oxidation of o-xylene and other hydrocarbons," *Applied Catalysis A: General* 157 (1997), pp. 263-310.

\* cited by examiner

PROCESS FOR CONTROLLING A GAS PHASE OXIDATION REACTOR FOR PREPARATION OF PHTHALIC ANHYDRIDE

CROSS-REFERENCE TO RELATED APPLICATIONS

This application claims benefit (under 35 USC 119(e)) of U.S. Provisional Application 61/323,409, filed Apr. 13, 2010 which is incorporated by reference.

BACKGROUND OF THE INVENTION

The invention relates to a process for controlling a gas phase oxidation reactor for preparation of phthalic anhydride.

Phthalic anhydride (PA) is prepared industrially by the catalytic gas phase oxidation of aromatic hydrocarbons, such as o-xylene and/or naphthalene, in fixed bed reactors. In general, a mixture of an oxygenous gas and the starting material to be oxidized is passed through tubes in which there is a bed of a catalyst. For temperature control, the tubes are surrounded by a heat carrier medium, for example a salt melt.

Even though the excess heat of reaction is removed by the heat carrier medium, local temperature maxima (hotspots) may develop in the catalyst bed, in which there is a higher temperature than in the remaining part of the catalyst bed. These hotspots lead to side reactions, such as the total combustion of the starting material, or to the formation of undesired by-products which are removable from the reaction product only with great difficulty, if at all.

The hotspot temperatures in the oxidation of o-xylene to phthalic anhydride are typically in the range between 400 and 500° C. Hotspot temperatures above 500° C. are an expression of increased total oxidation of the o-xylene to CO, $CO_2$ and water, and lead to increased damage to the catalyst. Excessively low hotspot temperatures are associated with insufficient conversion of o-xylene, and too high a content of disruptive underoxidation products, for example phthalide, which impairs the product quality. The hotspot temperature depends on a series of parameters, including the o-xylene loading of the gas stream, the loading of the catalyst with the gas stream, the service life of the catalyst, the heat transfer conditions in the reactor and in the salt bath, and the salt bath temperature.

The salt bath temperature is an important correcting parameter for the operation of the gas phase oxidation reactor. It is set correctly when overoxidation or total oxidation proceeds only to a small degree, and the product quality is impaired by underoxidation products to a minimum degree. Excessively high salt bath temperatures lead to falling PA yields and accelerated catalyst aging; excessively low salt bath temperatures result in poor product quality.

In modern plants, the salt bath temperature is controlled by a computer-based process control system, the aim of which is exact compliance with desired operating states. With the aid of mathematical models, the influence of the change of control parameters, such as the phthalic anhydride yield, the conversion of the aromatic hydrocarbon, a hotspot temperature and/or a content of at least one underoxidation product in the reaction product is assessed. Measured values for one or more control parameters are used to determine correcting interventions for control of the control parameter. In addition to the salt bath temperature, important correcting parameters include the loading of the gas stream with the hydrocarbon to be oxidized and the volume flow rate of the gas stream.

The activity of the catalysts or catalyst systems used for gas phase oxidation decreases with increasing operating time. One effect of the thermal stress in the region of the hotspot is the deactivation of the catalyst at the same point. A higher proportion of unconverted hydrocarbons or of partly oxidized intermediates gets into regions of the catalyst bed further downstream. The reaction shifts increasingly toward the reactor outlet and the hotspot migrates downstream. Since downstream catalyst layers are generally more active but less selective, undesired overoxidation and other side reactions increase. Overall, the product yield or selectivity falls with the operating time.

The catalyst deactivation can be counteracted to a limited degree by increasing the temperature of the heat carrier medium, typically at essentially constant hourly space velocity over the catalyst.

The service life of PA catalysts is typically about 5 years, the PA yield within this period decreasing by up to 6% by mass; cf. M. Galantowicz et al. in B. Delmon, G. F. Froment (eds.), Catalyst Deactivation 1994, Studies in Surface Science and Catalysis 88, Elsevier, p. 591-596. Typically, the salt bath temperature is raised by up to 40 K over the lifetime of the catalyst; cf. G. C. Bond, J. Chem. Tech. Biotechnol. 68 (1997) 6-13. For control of the salt bath temperature over a period of several years of catalyst lifetime, the prior art gives only a little information, especially for high catalyst hourly space velocities.

According to the disclosure of DE 2948163 (Nippon Shokubai), the PA yield is 113.8% by mass over a two-layer catalyst at an o-xylene loading of 83 $g/m^3$ (STP) after 2 months at a salt bath temperature of 370° C. After 12 months, at the same o-xylene loading but a salt bath temperature of 375° C., the PA yield decreases to 112.7% by mass. The salt bath temperature in this case was raised by 5 K within 10 months, i.e. by an average of 0.5 K/month.

Anastasov, Chemical Engineering and Processing 42 (2003) 449-460, studied the deactivation of a 04-26 $V_2O_5$/$TiO_2$ catalyst from BASF. At an o-xylene loading of 50 $g/m^3$ (STP), the PA yield of 79.9 mol % after 8.5 months at a salt bath temperature of 360° C. rose to 80.7 mol % after 24 months at the same o-xylene loading but a salt bath temperature of 370° C. The salt bath temperature was raised in this case by 10 K within 15.5 months, i.e. by an average of 0.65 K/month. The significant rise in the salt bath temperature by several kelvin per year is thus customary in the oxidation of o-xylene to PA.

A controlled process for temperature control of salt bath reactors for phthalic anhydride synthesis was described for the first time in DE 4109387 (Buna AG). The process comprises the determination of an optimal salt bath temperature from experimentally determined parameters, such as the hotspot temperature and the o-xylene concentration at the reactor inlet. The catalyst aging behavior is taken into account with a linear approach, which employs the apparent activation energy of the catalyst. The salt bath temperature is then adjusted in each case according to the optimal salt bath temperature determined. Depending on the operating conditions, this gives rise to increases or decreases in the salt bath temperatures. At an o-xylene loading of, for example, 43 $g/m^3$ (STP) after 282 days at a salt bath temperature of 376° C., the salt bath temperature was increased to 388° C. after 1470 days at a similar o-xylene loading of 42 $g/m^3$ (STP). This corresponds to an average increase in the salt bath temperature of 0.3 K/month. The optimal salt bath temperature determined after 1470 days of run time was 383° C., and thus 5 K lower. After a lowering of the salt bath temperature by 5 K, the PA yield rose from 65.5 to 71.8 mol %. The o-xylene concentration is included in the formula for determination of the optimal salt bath temperature. The o-xylene loadings reported in the examples are, however, comparatively low at 21-43 g/m³ (STP). In addition, a disadvantage of the method described is that the salt bath temperatures have to be adjusted very frequently.

EP-A 2 009 520 (Honeywell International Inc.) discloses a multivariable process control system for PA preparation. A catalyst performance-dependent first parameter and, as second parameter, the temperature at several positions in the reaction tube are measured. By means of a dynamic model, the temperature is adjusted automatically. The process is said to allow a dynamic adjustment of the temperature profile to compensate for catalyst aging.

BRIEF SUMMARY OF THE INVENTION

It is an object of the invention to specify a process for controlling a gas phase oxidation reactor for preparation of phthalic anhydride, in which the cumulated PA yield over the lifetime of the catalyst is maximized or, in other words, the decline in PA yield over the catalyst lifetime is minimized. The process should be suitable especially for high o-xylene loadings of 80-110 g/m³ (SW).

The object is achieved by a process for controlling a gas phase oxidation reactor for preparation of phthalic anhydride, by passing a gas stream which comprises an aromatic hydrocarbon and molecular oxygen through a multitude of reaction tubes arranged in the gas phase oxidation reactor, each of which comprises a bed of at least one catalyst and the temperature of which can be controlled by means of a heat transfer medium, at least one control parameter being measured and correcting interventions for control of the control parameter being determined, the at least one control parameter comprising the phthalic anhydride yield and the correcting parameter used being the temperature of the heat carrier medium. The process comprises limiting the change in the correcting parameter to a maximum of 0.5 K, preferably a maximum of 0.4 K, within a period of 30 days over at least 90% of the lifetime of the catalyst, preferably over 95% of the lifetime of the catalyst, especially over essentially the entire lifetime of the catalyst.

DETAILED DESCRIPTION OF THE INVENTION

The "lifetime of the catalyst" is understood to mean the time from the end of the startup of the reactor, i.e. from attainment of an essentially steady production state, until the shutdown of the reactor and exchange of the spent catalyst. The lifetime of the catalyst is typically several years.

The reactor used is preferably a salt bath-cooled tubular reactor. A heat carrier medium in the form of a salt bath flows around a tube bundle. The individual catalyst-filled tubes end in an upper tube plate and a lower tube plate. The reactor gas is generally passed through the tubes from the top downward, i.e. in the direction of gravity; however, a reverse flow direction is also conceivable. At the jacket of the reactor, there are ring channels spaced apart, through which the heat carrier medium is drawn off from the reactor and supplied back to the reactor after passing through a circulation pump. A substream of the heat carrier medium circulated is passed through a cooler in which, for example, saturated steam is produced. In the interior of the reactor, there may typically be baffle plates in order to impart a radial flow component to the heat carrier medium in the region of the tube bundle.

The heat carrier medium may pass through the tubular reactor either in cocurrent or in countercurrent in relation to the reaction gas.

According to the invention, the temperature of the heat carrier medium is increased by a maximum of 0.5, K within a period of 30 days. When the temperature of the heat carrier medium at a particular time x is, for example, $T_x$, the temperature for the time (x+30 days) is a maximum of ($T_x$+0.5 K). The change in the temperature of the heat carrier medium may be stepwise or continuous, but is preferably continuous. The derivative of the change in the temperature of the heat carrier medium with respect to time (i.e. the steepness of the temperature curve as a function of time) is preferably never greater than 0.5 K/30 days.

From the time of the first increase in the correcting parameter, i.e. in the temperature of the heat carrier medium, the correcting parameter is preferably a monotonously rising function of time. In other words, the correcting parameter is kept constant from the first increase, or is increased in the course of time. In other words, from the first increase, the temperature of the heat carrier medium is preferably not lowered again.

In general, the correcting parameter is increased by at least 2 K within a period of 365 days, in order to partly compensate for the catalyst deactivation.

The control parameter used is the phthalic anhydride yield. This is understood to mean the mass or amount of phthalic anhydride formed, based on the mass or amount of pure hydrocarbon used, for example o-xylene (feed of hydrocarbon×purity of the hydrocarbon). It is of course possible to measure further control parameters, for example the conversion of the aromatic hydrocarbon, a hotspot temperature and a content of at least one under-oxidation product in the reaction product, for example phthalide.

The salt bath temperature is generally controlled by a computer-based process control system. In one control unit, the influence of the change in a correcting parameter on one or more control parameters is recorded as a mathematical model or algorithm. The measured values of one or more control parameters are used to determine correcting interventions for control of the control parameter. Suitable models and programs which can be used to implement the present invention are familiar to those skilled in the art.

In addition to the temperature of the heat carrier medium, further correcting parameters can be varied. These include the loading of the gas stream with the hydrocarbon to be oxidized and the volume flow rate of the gas stream.

For heat removal, the heat carrier medium is circulated through a cooler with a pump. The cooler may be configured as a superheater of steam in a steam circuit. The temperature of the heat carrier medium can be influenced by varying the circulation rate and/or the amount of steam produced.

Even though the process according to the invention can be performed using a single catalyst, it is preferred that the reaction tubes comprise at least two catalyst layers arranged in succession in flow direction of the gas stream, the activities of the catalysts being different in adjacent catalyst layers.

A catalyst layer is considered in the present context to be the bed of a catalyst with essentially homogeneous activity, i.e. with essentially homogeneous composition of the active material, active material content and packing density (disregarding unavoidable fluctuations in the filling of the reactor). Successive catalyst layers thus differ in the activity of the catalysts present. The person skilled in the art is aware of various measures for controlling the catalyst activity, as explained below.

Activity of a catalyst or of a catalyst layer is understood to mean the conversion which is measured under identical conditions (especially with regard to catalyst volume, gas hourly space velocity (GHSV) or air rate, temperature of the heat carrier medium, hydrocarbon loading of the gaseous stream) in a test plant. The higher the conversion of a catalyst or of a catalyst layer, the higher the activity thereof. This method is suitable especially for comparison of activities or for determination of relative catalyst activities.

Where a plurality of catalyst layers are used, various configurations of the graduation of activity are possible. In a preferred embodiment, the activity of the catalysts increases constantly in flow direction of the gaseous stream from one catalyst layer to the next from the catalyst layer closest to the gas inlet to the catalyst layer closest to the gas outlet.

In another preferred embodiment, the gaseous stream is passed through more than three successive catalyst layers in flow direction of the gaseous stream; in this case, the activity of the catalysts increases from one catalyst layer to the next over a sequence of at least three of the catalyst layers in flow direction of the gaseous stream. For instance, it is possible, as the catalyst layer furthest upstream, to provide a relatively short, highly active catalyst layer, which is adjoined downstream by a less active catalyst layer, and this less active catalyst layer may be adjoined by further layers with activity rising stepwise.

The catalytically active material of the catalyst, in the case of use of different catalyst layers, preferably the catalytically active material of all catalysts, preferably comprises at least vanadium oxide and titanium dioxide.

Measures for controlling the activity of gas phase oxidation catalysts based on vanadium oxide and titanium dioxide are known per se to those skilled in the art. For instance, the catalytically active material may comprise compounds which, as promoters, influence the activity and selectivity of the catalyst. A further means of controlling the activity consists in the variation of the proportion of the active material or of the $V_2O_5$ content in the total weight of the catalyst, with higher active material or $V_2O_5$ contents causing a higher activity and vice versa.

The catalysts used in the process according to the invention are generally eggshell catalysts in which the catalytically active material is applied in the form of a shell to an inert support.

Typically, the titanium dioxide is used in the anatase form. The titanium dioxide preferably has a BET surface area of 15 to 60 m²/g, especially 15 to 45 m²/g, more preferably 13 to 28 m²/g. The titanium dioxide used may consist of a single titanium dioxide or a mixture of titanium dioxides. In the latter case, the value of the BET surface area is determined as the weighted mean of the contributions of the individual titanium dioxides. The titanium dioxide used consists, for example, advantageously of a mixture of a $TiO_2$ with a BET surface area of 5 to 15 m²/g and of a $TiO_2$ with a BET surface area of 15 to 50 m²/g.

The catalytically active material preferably comprises, based on the total amount of the catalytically active material, 1 to 40% by weight of vanadium oxide, calculated as $V_2O_5$, and 60 to 99% by weight of titanium dioxide, calculated as $TiO_2$. In preferred embodiments, the catalytically active material may additionally comprise up to 1% by weight of a cesium compound, calculated as Cs, up to 1% by weight of a phosphorus compound, calculated as P, and up to 10% by weight of antimony oxide, calculated as $Sb_2O_3$. All figures regarding the composition of the catalytically active material are based on the calcine state thereof, for example after calcination of the catalyst at 450° C. for one hour.

Suitable vanadium sources are particularly vanadium pentoxide or ammonium metavanadate.

Suitable antimony sources are various antimony oxides, especially antimony trioxide. In general, antimony trioxide with a mean particle size (maximum of the particle size distribution) of 0.1 to 10 µm is used. The source of the antimony oxide used in the first catalyst is more preferably particulate antimony trioxide with a mean particle size of 0.5 to 5 µm, especially 1 to 4 µm.

Vanadium and antimony may additionally also be used in the form of a vanadium antimonate compound. The vanadium antimonate incorporated in the active material of at least one layer can be prepared by reacting any desired vanadium and antimony compounds. Preference is given to the direct reaction of the oxides to give a mixed oxide or vanadium antimonate. The vanadium antimonate may have different molar ratios of V/Sb, and optionally also comprise further vanadium or antimony compounds and be used In a mixture with further vanadium or antimony compounds.

Useful phosphorus sources include especially phosphoric acid, phosphorous acid, hypophosphorous acid, ammonium phosphate or phosphoric esters, and in particular ammonium dihydrogenphosphate. Useful sources of cesium include the oxides or hydroxide, or the salts convertible thermally to the oxide, such as carboxylates, especially the acetate, malonate or oxalate, carbonate, hydrogencarbonate, sulfate or nitrate.

In addition to the optional additions of cesium and phosphorus, a multitude of other oxidic compounds may be present in small amounts in the catalytically active material, which, as promoters, influence the activity and selectivity of the catalyst, for example by lowering or increasing its activity. Examples of such promoters include the alkali metal oxides, especially, apart from the cesium oxide mentioned, lithium oxide, potassium oxide and rubidium oxide, thallium(I) oxide, aluminum oxide, zirconium oxide, iron oxide, nickel oxide, cobalt oxide, manganese oxide, tin oxide, silver oxide, copper oxide, chromium oxide, molybdenum oxide, tungsten oxide, iridium oxide, tantalum oxide, niobium oxide, arsenic oxide, antimony oxide, cerium oxide.

In addition, among the promoters mentioned, the oxides of niobium and tungsten are preferably useful as additives in amounts of 0.01 to 0.50% by weight, based on the catalytically active material.

The inert support material used may be virtually all prior art support materials, as used advantageously in the preparation of eggshell catalysts for the oxidation of aromatic hydrocarbons to aldehydes, carboxylic acids and/or carboxylic anhydrides, for example quartz ($SiO_2$), porcelain, magnesium oxide, tin dioxide, silicon carbide, rutile, alumina ($Al_2O_3$), aluminum silicate, steatite (magnesium silicate), zirconium silicate, cerium silicate or mixtures of these support materials. The support material is generally nonporous. The expression "nonporous" should be understood in the sense of "nonporous apart from technically inactive amounts of pores", since it is technically unavoidable that a small amount of pores may be present in the support material which ideally should not comprise any pores. Advantageous support materials which should be emphasized are especially steatite and silicon carbide. The form of the support material is generally not critical for the inventive precatalysts and eggshell catalysts. For example, catalyst supports can be used in the form of spheres, rings, tablets, spirals, tubes, extrudates or spall. The dimensions of these catalyst supports typically correspond to the catalyst supports typically used for preparation of eggshell catalysts for the gas phase partial oxidation of aromatic hydrocarbons. Steatite is preferably used in the form of spheres having a diameter of 3 to 6 mm or of rings having an external diameter of 5 to 9 mm and a length of 3 to 8 mm and a wall thickness of 1 to 2 mm.

The layer(s) of the eggshell catalyst are appropriately applied by spray application of a suspension of $TiO_2$ and $V_2O_5$, which optionally comprises sources of the abovementioned promoter elements, to the fluidized support. Before the coating, the suspension is preferably stirred for a sufficiently long period, for example 2 to 30 hours, especially 12 to 25 hours, in order to break up agglomerates of the suspended solids and to obtain a homogeneous suspension. The suspension typically has a solids content of 20 to 50% by weight. The suspension medium is generally aqueous, for example water itself or an aqueous mixture with a water-miscible organic solvent, such as methanol, ethanol, isopropanol, formamide and the like.

In general, organic binders, preferably copolymers, advantageously in the form of an aqueous dispersion, of acrylic acid/maleic acid, vinyl acetate/vinyl laurate, vinyl acetate/acrylate, styrene/acrylate and vinyl acetate/ethylene are added to the suspension. The binders are commercially available as aqueous dispersions with a solids content of, for example, 35 to 65% by weight. The amount of such binder dispersions used is generally 2 to 45% by weight, preferably 5 to 35% by weight, more preferably 7 to 20% by weight, based on the weight of the suspension.

The support is fluidized in, for example, a fluidized bed apparatus in an ascending gas stream, especially air. The apparatuses usually consist of a conical or spherical vessel in which the fluidizing gas is introduced from the bottom or from the top via an immersed tube. The suspension is sprayed into the fluidized bed via nozzles from the top, from the side or from the bottom. It is advantageous to use a riser tube arranged in the middle or concentrically around the immersed tube. Within the riser tube, there is a higher gas velocity which transports the support particles upward. In the outer ring, the gas velocity is only a little above the fluidization velocity. Thus, the particles are moved in a vertical cycle. A suitable fluidized bed apparatus is described, for example, in DE-A 4006935.

In the coating of the catalyst support with the catalytically active material, coating temperatures of 20 to 500° C. are generally employed, and the coating can be effected under atmospheric pressure or under reduced pressure. In general, the coating is effected at 0° C. to 200° C., preferably at 20 to 150° C., especially at 60 to 120° C. performed.

The catalytically active material can also be applied in two or more layers, in which case, for example, the inner layer has or the inner layers have an antimony oxide content of up to 15% by weight, and the outer layer has an antimony oxide content reduced by 50 to 100%. In general, the inner layer of the catalyst contains phosphorus and the outer layer is low in phosphorus or phosphorus-free.

The layer thickness of the catalytically active material is generally 0.02 to 0.2 mm, preferably 0.05 to 0.15 mm. The active material content in the catalyst is typically 5 to 25% by weight, usually 7 to 15% by weight.

As a result of thermal treatment of the precatalyst thus obtained at temperatures of more than 200 to 500° C., the binder escapes from the layer applied as a result of thermal decomposition and/or combustion. The thermal treatment is preferably effected in situ in the gas phase oxidation reactor.

The catalysts are introduced into reaction tubes which are thermostatted externally to the reaction temperature with a heat carrier medium, for example a salt melt. The gaseous stream is passed through the catalyst bed thus provided at temperatures of generally 300 to 450° C., preferably of 320 to 420° C. and more preferably of 340 to 400° C., and at a pressure of generally 0.1 to 2.5 bar gauge, preferably of 0.3 to 1.5 bar gauge, with a space velocity of generally 750 to 5000 $h^{-1}$.

The gas stream is generally obtained by mixing a gas which comprises molecular oxygen and, apart from oxygen, may also comprise suitable reaction moderators and/or diluents, such as steam, carbon dioxide and/or nitrogen, with the aromatic hydrocarbon to be oxidized. The gas comprising molecular oxygen generally comprises 1 to 100 mol %, preferably 2 to 50 mol % and more preferably 10 to 30 mol % of oxygen, 0 to 30 mol % and preferably 0 to 10 mol % of steam, and 0 to 50 mol % and preferably 0 to 1 mol % of carbon dioxide, remainder nitrogen.

The loading of the gas stream with the hydrocarbon to be oxidized is generally 30 g to 150 g per $m^3$ (STP) of gas, preferably 80 to 110 g per $m^3$ (STP). The hydrocarbon is preferably o-xylene, naphthalene or a mixture thereof, especially o-xylene.

The gas flow rate is generally 3.0 to 4.5 $m^3$ (STP)/h and tube, preferably 3.5 to 4.2 $m^3$ (STP)/h and tube.

It is possible to thermostat two or more zones, preferably two zones, of the catalyst bed present in the reaction tube to different reaction temperatures, for which it is possible, for example, to use reactors with separate salt baths. Alternatively, the gas phase oxidation can also be performed without division into temperature zones at one reaction temperature.

The invention is illustrated in detail by the examples which follow.

The catalysts which follow were prepared according to the description in WO 2007/116018 described. All figures regarding the composition of the active material (in % by weight) and the active material content (based on the total weight of the catalyst) are based on the calcined state thereof, i.e. after calcination of the catalyst at 450° C. for one hour.

Catalyst KL1:
Active material content: 9.1%. Composition of the active material: 7.1% $V_2O_5$, 1.8% $Sb_2O_3$, 0.38% Cs, remainder $TiO_2$ with a BET surface area of 16 $m^2/g$.

Catalyst KL2:
Active material content: 8.5%. Composition of the active material: 7.95% $V_2O_5$, 2.7% $Sb_2O_3$, 0.31% Cs, remainder $TiO_2$ with a BET surface area of 18 $m^2/g$.

Catalyst KL3:
Active material content: 8.5%. Composition of the active material: 7.1% $V_2O_5$, 2.4% $Sb_2O_3$, 0.10% Cs, remainder $TiO_2$ with a BET surface area of 17 $m^2/g$.

Catalyst KL4:
Active material content: 9.1%. Composition of the active material: 20% $V_2O_5$, 0.38% P, remainder $TiO_2$ with a BET surface area of 23 $m^2/g$.

The catalytic oxidation of o-xylene to phthalic anhydride was performed in a salt bath-cooled 15105 tubular reactor with an internal diameter of the tubes of 25 mm. To record temperature profiles, some reactor tubes were equipped with a thermocouple. 4.0 $m^3$ (STP) of air per hour with o-xylene (purity about 99% by mass) from 0 to 100 $g/m^3$ (STP) were passed through the tubes. The PA yields were measured in the reactor outlet gas and are reported in % by mass (kg of PA per kg of o-xylene converted), based on 100% o-xylene.

Example 1a (Noninventive)

KL1/KL2/KL3/KL4 bed length distribution 128 cm/67 cm/58 cm/58 cm (reactor length 330 cm)

After 288 days of run time, the salt bath temperature was raised at constant o-xylene loading. The salt bath temperature was raised in a linear manner in each case from days 288-391, 391-463 and 463-688. After 688 days, the salt bath temperature was 350.6° C. The PA yield fell within this period from 113.9 to 112.6%. Overall, this corresponds to a rise in the salt bath temperature by 0.37 K/month (1 month=30 days) and a decline in PA yield of 1.2% by mass/a.

| Run time [d] | Loading [g/m³ (STP)] | Salt bath temperature [° C.] | PA yield [% by ma.] |
|---|---|---|---|
| 288 | 97 | 345.7 | 113.9 |
| 391 | 97 | 348.1 | 113.3 |
| 463 | 97 | 348.1 | 113.2 |
| 688 | 97 | 350.6 | 112.6 |

Analyzing the profile of the salt bath temperature against time and the yield profile against time in more detail gives the following picture:

| Run time [d] | Loading [g/m³(STP)] | Salt bath temperature | PA yield |
|---|---|---|---|
| 288-391 | 97 | +0.71 K/month | −2.1% by ma./a |
| 391-463 | 97 | +/−0 K/month | −0.5% by ma./a |
| 463-688 | 97 | +.034 K/month | −1.0% by ma./a |

A rise in the salt bath temperature between 0 and 0.5 K/30 days is clearly particularly advantageous. When the salt bath temperature is raised more rapidly, the PA yield declines significantly more rapidly.

Example 1b (Inventive)

KL1/KL2/KL3/KL4 bed length distribution 130 cm/88 cm/58 cm/44 cm (reactor length 340 cm)

In this example, the salt bath temperature was raised after 189 days of run time. After 694 days, the salt bath temperature was 352.7° C. The PA yield fell within this period from 114.3 to 112.2% with a simultaneous increase in the o-xylene loading from 91 to 95 g/m³ (STP).

Overall, this corresponds to an increase in the salt bath temperature by 0.36 K/month and a decline in PA yield of 1.5% by mass/a.

| Run time [d] | Loading [g/m³ (STP)] | Salt bath temperature [° C.] | PA yield [% by ma.] |
|---|---|---|---|
| 189 | 91 | 346.8 | 114.3 |
| 694 | 95 | 352.7 | 112.2 |

Example 2 (Noninventive)

KL1/KL2/KL3/KL4 bed length distribution 121.5 cm/80 cm/60 cm/58 cm (reactor length 340 cm)

In this example, the salt bath temperature was raised after 314 days with constant o-xylene loading. After 614 days, the salt bath temperature was 352.0° C. The PA yield fell within this period from 113.4 to 110.6%. Overall, this corresponds to an increase in the salt bath temperature by 0.54 K/month and a decline in PA yield of 3.4% by mass/a.

| Run time [d] | Loading [g/m³ (STP)] | Salt bath temperature [° C.] | PA yield [% by ma.] |
|---|---|---|---|
| 314 | 90 | 346.7 | 113.4 |
| 458 | 90 | 349.5 | 113.3 |
| 477 | 90 | 348.3 | 112.9 |
| 611 | 90 | 352.8 | 110.9 |
| 614 | 90 | 352.0 | 110.6 |

Analyzing the profile of the salt bath temperature against time and the yield profile against time in more detail gives the following picture:

| Run time [d] | Loading [g/m³(STP)] | Salt bath temperature | PA yield |
|---|---|---|---|
| 314-458 | 90 | +0.6 K/month | −0.25% by ma./a |
| 458-477 | 90 | −1.3 K/month | −8.0% by ma./a |
| 477-611 | 90 | +1.0 K/month | −5.4% by ma./a |
| 611-614 | 90 | −8.1 K/month | −3.1% by ma./a |

The more rapidly the salt bath temperature is raised, the more rapid is the decline in PA yield. Surprisingly, lowering the salt bath temperature cannot increase the PA yield again. On the contrary, lowering the salt bath temperature with stable o-xylene loading actually results in a further decline in yield.

The invention claimed is:

1. A process for controlling a gas phase oxidation reactor for preparation of phthalic anhydride, which comprises passing a gas stream which comprises an aromatic hydrocarbon and molecular oxygen through a multitude of reaction tubes arranged in the gas phase oxidation reactor, each of which comprises a bed of at least one catalyst and the temperature of which can be controlled by means of a heat transfer medium, at least one control parameter being measured and correcting interventions for control of the control parameter being determined, the at least one control parameter comprising the phthalic anhydride yield and the correcting parameter used being the temperature of the heat transfer medium, which comprises limiting the change in the correcting parameter to a maximum of 0.4 K within a period of 30 days over at least 95% of the lifetime of the catalyst, wherein the loading of the gas stream which comprises an aromatic hydrocarbon is 90 to 110 g/m³(STP).

2. The process according to claim 1, wherein the correcting parameter is a monotonously rising function of time from the time of the first increase in the correcting parameter.

3. The process according to claim 1, wherein the correcting parameter is increased by at least 2 K within a period of 365 days.

4. The process according to claim 1, wherein the at least one control parameter also comprises a control parameter selected from the conversion of the aromatic hydrocarbon, a hotspot temperature and a content of at least one underoxidation product in the reaction product.

5. The process according to claim 1, wherein the hydrocarbon is o-xylene, naphthalene or a mixture thereof.

6. The process according to claim 1, wherein the catalytically active material of the catalyst comprises at least vanadium oxide and titanium dioxide.

7. The process according to claim 1, wherein the reaction tubes comprise at least two catalyst layers arranged in succession in flow direction of the gas stream, the activities of the catalysts in adjacent catalyst layers being different from one another.

8. The process according to claim 1, wherein the hydrocarbon is o-xylene.

* * * * *